United States Patent [19]

Enomoto et al.

[11] Patent Number: 5,001,100

[45] Date of Patent: Mar. 19, 1991

[54] CATALYST USED IN A PROCESS FOR PRODUCING PYROMELLITIC DIANHYDRIDE

[75] Inventors: Norihide Enomoto; Yoshihiro Naruse, both of Chiba, Japan

[73] Assignee: Kawasaki Steel Corporation, Chiba, Japan

[21] Appl. No.: 484,396

[22] Filed: Feb. 23, 1990

Related U.S. Application Data

[62] Division of Ser. No. 314,367, Feb. 22, 1989, Pat. No. 4,925,957.

[30] Foreign Application Priority Data

Feb. 24, 1988 [JP] Japan .................................. 63-39472

[51] Int. Cl.$^5$ ........................ B01J 21/06; B01J 23/04; B01J 23/22; B01J 23/28
[52] U.S. Cl. ................................... 502/178; 502/309; 502/312

[58] Field of Search ............... 502/178, 309, 312, 320, 502/322, 317, 305, 324

[56] References Cited

U.S. PATENT DOCUMENTS

| | | | |
|---|---|---|---|
| 4,259,211 | 3/1981 | Krabetz et al. | 502/178 |
| 4,415,752 | 11/1983 | Decker et al. | 502/312 |
| 4,892,856 | 1/1990 | Kawajiri et al. | 502/312 |

*Primary Examiner*—W. J. Shine
*Attorney, Agent, or Firm*—Bierman and Muserlian

[57] ABSTRACT

A catalyst comprising an inert support that carries on it vanadium oxide, sodium oxide and molybdenum oxide in predetermined amounts, at least one additional component in a predetermined amount which is selected from among chromium oxide, manganese oxide, niobium oxide and titanium oxide is capable of producing pyromellitic dianhydride in high yield from inexpensive durene over a broad optimal temperature range while suppressing the generation of heat in the catalyst bed.

5 Claims, 2 Drawing Sheets

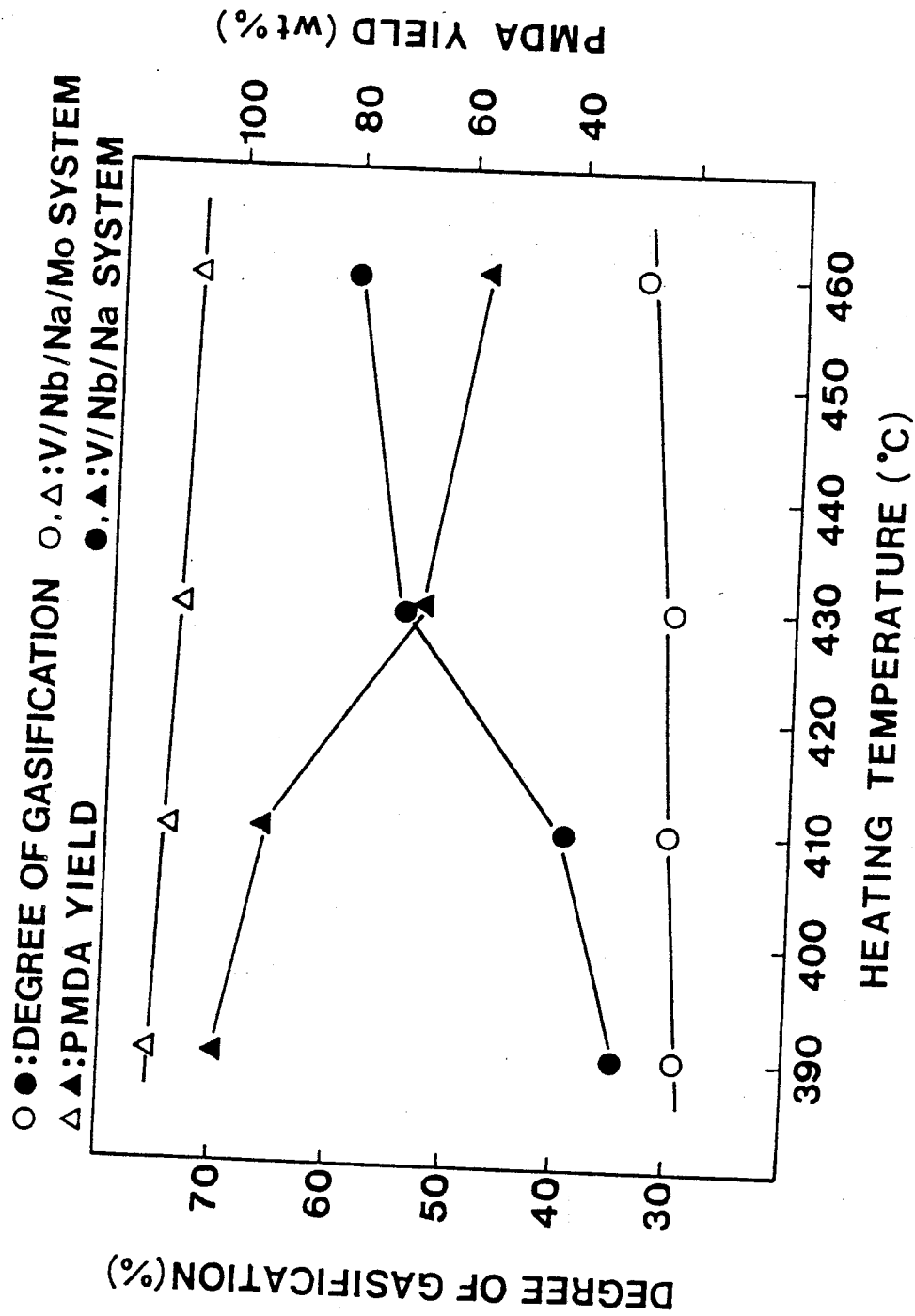

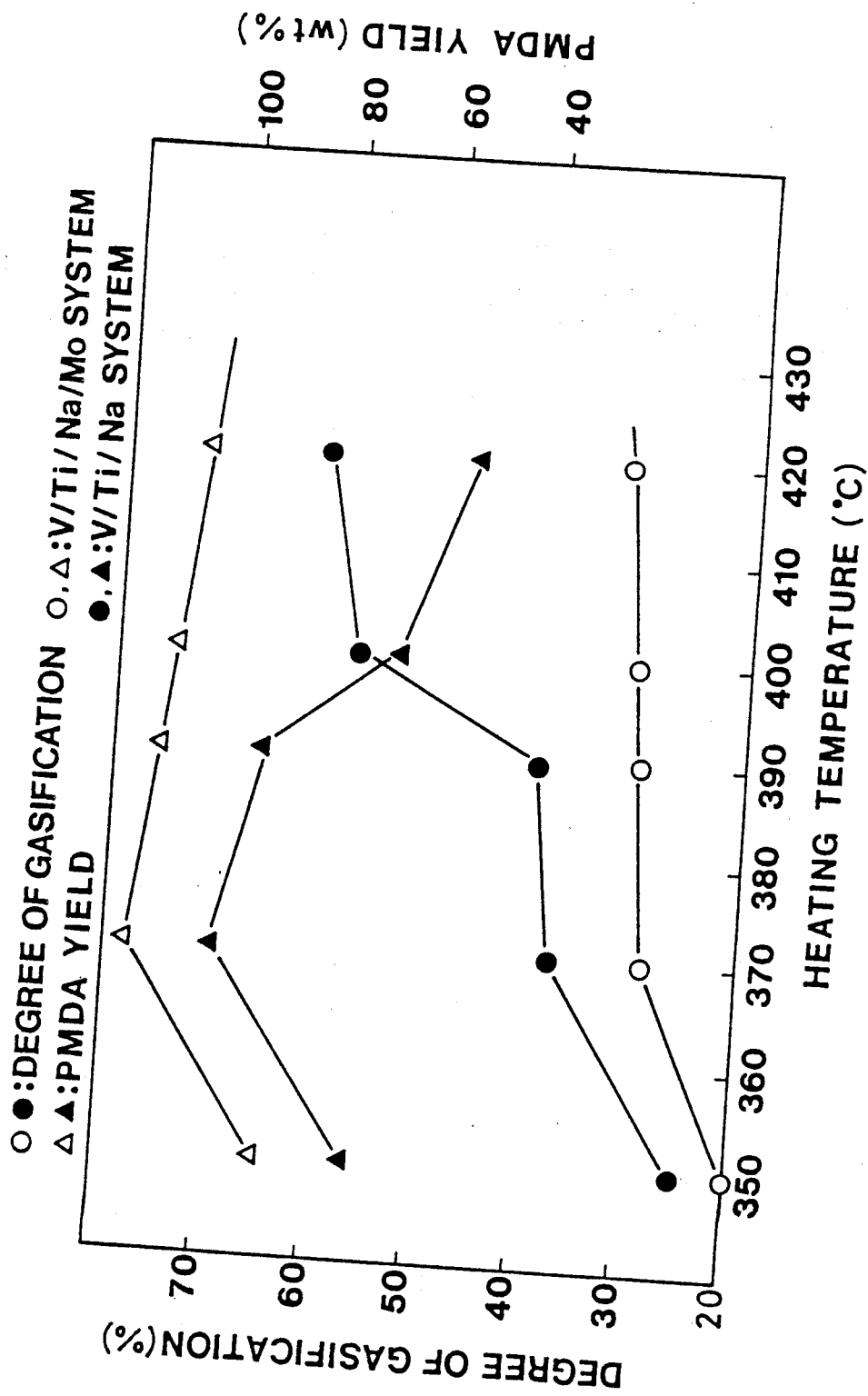

CATALYST USED IN A PROCESS FOR PRODUCING PYROMELLITIC DIANHYDRIDE

This is a division of application Ser. No. 314,367, filed Feb. 22, 1989, now U.S. Pat. No. 4,925,957.

BACKGROUND OF THE INVENTION

The present invention relates to a process for producing pyromellitic dianhydride from 1,2,4,5-tetramethylbenzene(durene) by vapor-phase catalytic oxidation with a gas containing molecular oxygen. The present invention also relates to a catalyst used in this process.

Pyromellitic dianhydride (PMDA) has been used extensively as raw material for heat-resistant resins or as a plasticizer or a curing agent for epoxy resins. More recently, the potential for producing durene at a lower cost using an alkylation catalyst such as zeolite has increased and there is a growing interest in the importance of PMDA as an industrial raw material.

PMDA can be synthesized by either liquid-phase oxidation(oxidation with nitric acid or a cobalt acetate-sodium bromide system) or vapor-phase catalytic oxidation using a catalyst. For small-scale production, liquid-phase oxidation is suitable and is the principal commercial method used today. However, in view of the growing demand for PMDA, vapor-phase catalytic oxidation which is suitable for large-scale production is anticipated to become a predominant commercial process to be adopted in the future.

In PMDA production from durene by vapor-phase catalytic oxidation, a catalytic component based vanadium pentoxide is carried on a support such as fused alumina ($\alpha$-alumina) or silicon carbide (these materials have a specific surface area of no larger than 1 m$^2$/g) and is used as a catalyst. A catalyst solely composed of vanadium pentoxide on a support may be used in PMDA production but suffers from various disadvantages such as formation of by-products in large quantities, low conversion and low yield of PMDA. To avoid these problems, it is a common practice to use a catalyst that is based on vanadium pentoxide which, in combination with additional catalytic components selected from oxides (chiefly metal oxides), is carried on a support. Examples of this catalyst are described in many patents such as Japanese Patent Publication Nos. 42-1008, 42-15925, 43-26497, 45-4978, 45-15018, 45-15252, 46-14332, 49-31972 and 49-31973. However, if these prior art catalysts are used in a fixed-bed reactor which is adopted customarily in industrial catalytic reactions, the high sensitivity of the reaction to temperature causes the following problems. In commercial production of PMDA, a reaction tube typically having a diameter of 1 inch is filled with ca. 0.5–2 liters of a catalyst and submerged in a molten salt bath, with durene supplied into the reaction tube from the top together with a molecular oxygen containing gas(normally air). In the catalyst bed, molecular oxygen reacts with durene by the catalytic action to produce PMDA. At the same rime, part of the durene feed undergoes excessive reaction and is completely oxidized to evolve gases such as carbon dioxide and carbon monoxide.

The catalysts disclosed in the above-listed prior patents have high reactivity and may produce PMDA with high selectivity but even in this case, the conversion to gases (i.e. CO$_2$ and CO) is high and cannot be reduced to 35% or below. Furthermore, the prior art catalyst systems have great temperature dependency and the conversion to oxidized gases increases rapidly if the reaction temperature is outside an optimal range. To make the case worse, the optimal range of reaction temperature is very narrow (20°–30° C).

When the catalyst is packed in the reaction tube, the catalyst bed will be as high as 60–200 cm and a temperature distribution will inevitably occur on account of the heat of reaction. The heat of reaction under consideration is 560 kcal/mol, which is considerably greater than that of the reaction involved in producing phthalic anhydride from orthoxylene or naphthalene. Theoretically, the heat of reaction generated in the production of PMDA from durene is no less than 1.8 times the heat of reaction generated in producing phthalic anhydride from orthoxylene. If durene is completely gasified to carbon dioxide or carbon monoxide, the amount of heat generated will even exceed 1,100 kcal/mol. Therefore, the reaction under consideration which will inherently generate more heat than other partial oxidation reactions has a tendency to create a broader temperature distribution in the catalyst bed. On top of this, if known catalysts are used, 35% or more conversion to gases will occur, which leads to an even broader temperature distribution in the catalyst bed that is out side the optimal temperature range for the catalyst. Then, a vicious cycle starts and an increased conversion to gases will reduce the yield of PMDA.

Various efforts have been made to remove the heat of reaction from the catalyst bed but from an engineering aspect of the reaction involved, the approaches that can be taken are limited and there has been no alternative to performing the reaction while sacrificing the production rate by reducing the concentration of durene feed, the height of the catalyst bed or the diameter of the reaction tube. In order to solve the aforementioned problems completely, it is important to develop a catalyst that has a high selectivity for PMDA with a small conversion to gases and which can be used over a broad optimal reaction temperature range. The use of such an ideal catalyst will facilitate temperature control in the catalyst bed and increase the efficiency of PMDA production.

SUMMARY OF THE INVENTION

An objection, therefore, of the present invention is to provide an industrially advantageous process by which pyromellitic dianhydride(PMDA) can be produced in high yield over a broad optimal reaction temperature range with the degree of gasification(evolution of carbon dioxide and carbon monoxide) and the heat of reaction being reduced to low levels.

Another object of the present invention is to provide a catalyst suitable for use in the above-described process.

To attain these objects, the present invention provides a catalyst for use in the production of pyromellitic dianhydride that comprises an inert support carrying vanadium oxide, sodium oxide, molybdenum oxide, and at least one additional component selected from among chromium oxide, manganese oxide, niobium oxide and titanium oxide, with the atomic ratios of the metallic elements in the supported oxides being within the following ranges: Na/V=0.1/10–1.0/10, Mo/V=0.3/10–3.0/10, Cr/V=0.2/10–2.0/10, Mn/V=0.1/10–1.5/10, Nb/V=0.5/10–3.0/10, and Ti/V=0.1/10–1.0/10. The present invention also provides a process for producing pyromellitic dianhydride by vapor-phase catalytic oxidation of durene in the presence of this catalyst.

BRIEF DESCRIPTION OF THE DRAWINGS

FIG. 1 is a graph showing the results obtained in Examples 10-13 and Comparative Examples 4-7 to be described hereinafter; and FIG. 2 is a graph showing the results obtained in Examples 14-18 and Comparative Examples 8-12 to be also described hereinafter.

DETAILED DESCRIPTION OF THE INVENTION

First, the process for producing pyromellitic dianhydride in accordance with the present invention is described hereinafter. In the process of the present invention, 1,2,4,5,-tetramethylbenzene(durene) is subjected to vapor-phase catalytic oxidation with a molecular oxygen containing gas using the catalyst to be described below, preferably in a fixed-bed reactor, to produce pyromellitic dianhydride.

If a fixed-bed reactor is to be used, the reaction tube to be packed with a catalyst may have an inside diameter of about 1 inch. In production at a commercial scale, the reaction is performed with 0.5-2.0 liters of the catalyst packed into the reaction tube. Optimal values of reaction conditions for commercial-scale production can be determined by performing calculations based on various parameters including the reaction rate, material transfer rate, heat transfer rate and the physical properties of individual fluids and solids using the computer program developed by the present inventors.

The reaction involved in the process of the present invention can be performed at a high space velocity in the range of 8,000-15,000$h^{-1}$. The reaction can be performed at a space velocity higher than 15,000$h^{-1}$ but this is not very advantageous since an increased pressure loss will occur in the catalyst bed. If the space velocity decreases, even the catalyst of the present invention is not immune to increased conversion to gasification. Furthermore, the supply of feed material per unit time is reduced, which is not advantageous from a productivity viewpoint. Therefore, an optimal range of space velocity lies between 10,000 and 14,000$h^{-1}$.

When the durene concentration of feed gas (for example; air) exceeds 0.25 mol%, the heat of oxidation reaction increases rapidly. Special equipment is required to reduce the increased temperature of the catalyst bed.

The durene concentration less than 0.mol% is not advantageous from a productivity view point.

Therefore the durene concentration of feed gas is preferably 0.1-0.25 mol%.

The optimal temperature for the catalyst bed varies with the composition of the catalyst and the catalyst of the present invention is not an exception. In addition, differing concentrations of durene which is the feed material allow heat to be generated in different amounts in the catalyst bed, and differing space velocities cause differences in the rates of material transfer and heat transfer. Therefore, no general statement can be made for the optimal temperature for the catalyst and only guide FIGURES can be given according to the catalyst composition: for a catalyst containing titanium oxide, a comparatively low temperature range is preferred with the initial setting of heating temperature(i.e., the temperature of a heating medium for the catalyst bed) being at 360-420° C. and the maximum temperature of the catalyst bed at 415-475° C.; for a catalyst containing niobium oxide, a comparatively high temperature range is preferred with the setting of heating temperature being at 390-460° C. and the maximum temperature of the catalyst be at 435-510° C. Therefore, using the catalyst of the present invention, the intended reaction can be performed over a broad temperature range(360°-460° C. for the setting of heating temperature, and 415°-510° C. for the maximum temperature of the catalyst bed). At temperatures below the lower limit of this range, the activity of the catalyst decreases to reduce the yield of PMDA. If the catalyst is used at temperatures exceeding the upper limit of the above-said range, the conversion to gases will exceed the appropriate level, causing a decrease in the yield of PMDA.

The catalyst of the present invention is described below in a more specific way. This catalyst comprises an inert support carrying vanadium oxide, sodium oxide, molybdenum oxide, and at least one additional component selected from among chromium oxide, manganese oxide, niobium oxide and titanium oxide, with the atomic ratios of the metallic elements in the supported oxides being in the following ranges: Na/V=0.1/10-1.0/10, Mo/V=0.3/10-3.0/10, Cr/V=0.2/10-2.0/10, Mn/V=0.1/10-1.5/10, Nb/V=0.5/10-3.0/10, and Ti/V=0.1/10-1.0/10.

The catalyst described above is a novel catalyst suitable for use in the production of pyromellitic dianhydride and is the product of the following studies conducted by the present inventors. Vanadium pentoxide used as the sole catalyst component does not have sufficient activity or reactivity to produce good results in the production of pyromellitic dianhydride. It is, therefore, the usual practice to add various cocatalyst components (metal oxides) but the activity and reactivity of the resulting catalyst are greatly influenced by the type and amount of the cocatalyst component added. A catalyst containing $V_2O_5$, $CrO_3$ and $Na_2O$ as catalyst components and which is carried on a support such as $\alpha$-alumina or silicon carbide that has a specific surface area of no more than 1$m^2$/g and a particle size of 3-6 mm$\phi$ exhibits high activity when the atomic ratios of Cr and Na to vanadium are within the ranges of 0.2/10-2.0/10 (Cr/V) and 0.1/10-1.0/10 (Na/V), and pyromellitic dianhydride can be produced in high yield (100% on a weight basis).

However, if the atomic ratios of Cr and Na to vanadium are outside their appropriate ranges specified above, various problems occur such as low yield of pyromellitic dianhydride. Even if these atomic ratios are within the appropriate ranges, more than 35% of durene feed will be gasified and detected as carbon dioxide or carbon monoxide. If such a gasification occurs heavily in a commercial operation using a large amount of catalyst, an increased amount of heat will be generated during the reaction and difficulty is encountered in controlling the removal of heat. Therefore, from a practical viewpoint, the gasification of durene due to its complete combustion which is accompanied by severe heat generation should be reduced to the lowest possible level.

Given the same levels of conversion and selectivity to PMDA, an ideal catalyst that is advantageous for use in commercial production of PMDA should allow to reduced degree of gasification (in terms of the percentage of durene converted to $CO_2$ and CO) from the viewpoints of reaction temperature control and catalyst's life. Based on this understanding, the present inventors conducted intensive studies and found that by adding $MoO_3$ (molybdenum oxide) to the catalyst composition consisting of $V_2O_5$, $CrO_3$ and $Na_2O$, a catalyst could be obtained that was capable of producing PMDA in high yield over a broad optimal range of reaction temperatures and which yet ensured a low level of conversion to gases such as $CO_2$ and CO during the reaction. The present invention has been accomplished on the basis of this finding.

The appropriate amount of molybdenum addition is such that the atomic ratio of Mo to V atom is in the range of 0.3/10–3.0/10. If the molybdenum content is less than 0.3/10 in terms of Mo/V atomic ratio, the effect of molybdenum addition is not fully exhibited and in case of a high-activity catalyst that is capable of PMDA production in a yield higher than 98 wt. % (60 mol%), more than 35% of the durene feed will be gasified (the degree of gasification is more than 35%). If the molybdenum content exceeds 3.0/10 in terms of Mo/V atomic ratio, the degree of gasification is certainly reduced to 30% and below but at the same time, the activity of the catalyst is also reduced, leading to a lower yield of PMDA. In the range of Mo/V=0.3/10–3.0/10, the yield of PMDA is comparable to or slightly better than the level attained when molybdenum is not added. As a result of reduction in the degree of gasification, intermediate oxides which are the products of partial oxidation of durene will be formed in somewhat increased amounts but these intermediates, being different from PMDA in physical properties such as vapor pressure, can be readily separated from PMDA and hence will cause no significant problems. Accordingly, the preferred composition of the $V_2O_5$-$CrO_3$-$Na_2O$-$MoO_3$ catalyst is such that the atomic ratios of Cr, Na and Mo to vanadium atom are Cr/V=0.2/10–2.0/10, Na/V=0.1/10–1.0/10, and Mo/V=0.3/10–3.0/10.

The present inventors also found that industrially useful catalyst compositions could also be produced by adding molybdenum oxide ($MoO_3$) to $V_2O_5$-$MnO_2$-$Na_2O$, $V_2O_5$-$Nb_2O_5$-$Na_2O$, and $V_2O_5$-$TiO_2$-$Na_2O$ systems. The resulting catalysts can be used with a good catalytic activity in PMDA production and the degree of gasification is reduced with a corresponding decrease in the resulting heat generation.

As in the case of the $V_2O_5$-$CrO_3$-$Na_2O$-$MoO_3$ catalyst, the catalysts of $V_2O_5$-$MnO_2$-$Na_2O$-$MoO_3$, $V_2O_5$-$Nb_2O_5$-$Na_2O$-$MoO_3$ and $V_2O_5$-$TiO_2$-$Na_2O$-$MoO_3$ systems have preferred compositional ranges that are expressed as follows in terms atomic ratios to vanadium atom: Mn/V=0.1/10–1.5/10, Na/V=0.1/10–1.0/10, and Mo/V=0.3/10–3.0/10, for the $V_2O_5$-$MnO_2$-$Na_2O$-$MoO_3$ system: Nb/V=0.5/10–3.0/10, Na/V=0.1/10–1.0/10, and Mo/V=0.3/10–3.0/10 for the $V_2O_5$-$Nb_2O_5$-$Na_2O$-$MoO_3$ system; and Ti/V=0.1/10–1.0/10, Na/V=0.1/10–1.0/10, and Mo/V=0.3/10–3.0 for the $V_2O_5$-$TiO_2$-$Na_2O$-$MoO_3$ system.

The catalyst components described above are carried on an inert support which is preferably selected from among fused alumina($\alpha$-alumina), silicon carbide, cordierite, etc. The catalyst components will fully exhibit the intended catalytic activity if vanadium pentoxide is considered in a weight ranging from 3 to 15% by weight of the support.

While molybdenum oxide is an appropriate catalytic component, a binary system composed of vanadium oxide and molybdenum oxide or a ternary system composed of vanadium oxide, molybdenum oxide and phosphorus oxide will exhibit little or no catalytic activity. Even if they exhibit some catalytic activity, they are effective only in a low-productivity region where the space velocity is $5,000h^{-1}$ and below.

Vanadium pentoxide based complex oxide catalysts containing molybdenum which are suitable for used in PMDA production in accordance with the present invention may be preferably prepared by the following process. Vanadium pentoxide or ammonium metavanadate is used as a vanadium source. Since these compound are only slightly soluble in water, an organic acid is added to render them water-soluble. The organic acid is added in an amount 0.5–2.0 times the equivalent of V atom and suitable organic acids are oxalic acid and tartaric acid.

Substances serving as cocatalyst(additional) components are then added to an aqueous solution of the vanadium source. They may be in the form of a metal oxide or a metal salt (e.g. ammonium salt, carbonate, chloride, nitrate or oxalate) and any form can be employed with little problem occurring in practical applications so long as they are water soluble and become metal oxides at 400°–500° C. In the case where titanium oxide is to be used as a cocatalyst component, some Ti sources such as anatase titanium oxide, alkoxytitanium compound and titanium hydroxide may assume a slurry form but these can be used per se without any problem. The so prepared aqueous solution of catalyst components are then worked to be carried either on a support such as fused alumina ($\alpha$-alumina) or silicon carbide that preferably have a particle size of 2–5 mm$\phi$ and a specific surface area of no greater than $1m^2/g$ or on a honeycomb support that is made of fused alumina or cordierite and which has at least 100 passage-ways per square inch for gas penetration.

The catalyst components may be supported by the impregnation method in which a solution containing not only the catalyst components but also a support is concentrated to dryness or by spraying the catalyst solution onto a preheated support. The impregnation method would be advantageous for a support such as $\alpha$-alumina having a high porosity, and the spray method is advantageous for a support such as silicon carbide having a low porosity.

The catalyst thus formed of the catalyst components carried on the support is calcined at 500° C. for 3–8h under an air stream and subjected to a reaction experiment.

The performance of the catalyst is evaluated by the following method: ca. 60 cc of the catalyst is packed in a reaction tube having an inside diameter of 1 inch; the reaction tube is submerged in a molten salt bath at 350–500° C. and durene is supplied in to the tube to perform oxidation reaction at a space velocity (SV) of, $3,000-15,000h^{-1}$ and at a durene to air molar ratio of 0.1–0.4% the reaction product is converted to methyl ester forms by treatment with a methanol containing methanol-boron trifluoride complex salt and analyzed by gas chromatography; in addition, the reaction gases produced are withdrawn with a syringe and analyzed by gas chromatography.

The following examples are provided for the purpose of further illustrating the present invention but are by no means intended to be limiting.

EXAMPLE 1

Water (200 cc) was added to vanadium pentoxide (6.0 g) and oxalic acid (16.6 g), and the mixture was held in a hot water bath. To the heated mixture, ammonium chromate (0.5 g), sodium carbonate (174 mg) and molybdic acid (593 mg, 80 wt. % $MoO_3$) were added to prepare an aqueous solution of catalyst components. To this solution, Δ-alumina (60 g; particle size, 3 mmφ) was added and the mixture was concentrated to dryness over a hot water bath with careful stirring. The dried mixture was calcined at 500° C. for 3h under an air stream to prepare a catalyst consisting of 10V, 0.5 Cr, 0.5 Na and 0.5 Mo in atomic ratio.

The prepared catalyst (60 cc) was packed into a reaction tube having an inside diameter of 1 inch. After immersing the reaction tube in a molten salt bath, a reaction experiment was conducted in the following manner. A feed gas consisting of durene and air at a molar ratio of 0.2:100 was supplied into the reaction tube from the top at a space velocity of 12,000$h^{-1}$ while the molten salt bath was held at 400° C. During the reaction, the temperature of the catalyst bed reached a maximum of 437° C. The reaction gases being generated were withdrawn with a syringe and analyzed by gas chromatography; 29% of durene was found to have been gasified.

As a result of the reaction, pyromellitic dianhydride (PMDA) was produced in a yield of 113 wt. % (based on the weight of durene). The reaction product was analyzed by the following method: when ca. 5g of the reaction product was formed, methanol (40 cc) containing a methanol-boron trifluoride complex salt was added to the reaction product and the mixture was refluxed for 1h to convert the pyromellitic dianhydride to methyl ester forms; chloroform (30 cc) and water (20 cc) were added to have the methyl ester compound extracted in the chloroform layer; and the chloroform layer was analyzed by gas chromatography.

EXAMPLE 2

A reaction experiment was conducted as in Example 1 except that the molten salt bath was held at 430° C.

EXAMPLE 3

A reaction experiment was conducted as in Example 1 except that the molten salt bath was held at 440° C. and that the concentration of durene in the feed gas (in mol% of air) was adjusted to 0.22.

The results of Examples 1-3 are shown in Table 1, from which one can see that the catalyst systems used in these examples are industrially advantageous catalysts since the initial setting of heating temperature could be altered without causing any significant change in the yield of PMDA.

TABLE 1

| | Heating temperature (temperature of molten salt bath) (°C.) | Maximum temperature (°C.) | Space velocity $h^{-1}$ | Durene concentration mol % (of air) | PMDA yield (wt %) | Degree of gasification ($CO_2$ + CO/durene) (%) |
|---|---|---|---|---|---|---|
| Example 1 | 400 | 437 | 12,000 | 0.20 | 113 | 29 |
| Example 2 | 430 | 474 | 12,000 | 0.20 | 107 | 32 |
| Example 3 | 440 | 488 | 12,000 | 0.22 | 105 | 33 |

COMPARATIVE EXAMPLE 1

A catalyst was prepared as in Example 1 except that molybdic acid was not added. The so prepared catalyst was used in a reaction experiment that was conducted as in Example 1. During the reaction, the temperature of the catalyst bed reached a maximum of 452° C. The reaction gases being generated were withdrawn with syringe and analyzed by gas chromatography; 39% of durene was found to have been gasified.

As a result of the reaction, pyromellitic dianhydride was produced in a yield of 95 wt. %.

Comparing these results with those obtained in Example 1, one can see that by adding molybdenum to the catalyst, the reaction temperature in the catalyst bed was lowered by as many as 15° C. while the degree of gasification of durene decreased by 10%.

EXAMPLES 4-7 AND COMPARATIVE EXAMPLE 2

Catalysts were prepared as in Example 1 except that the amount of molybdic acid addition was changed. The so prepared catalysts were used in reaction experiments, the results of which are shown in Table 2 together with those of Example 1 and Comparative Example 1.

The data in Table 2 shows that through addition of molybdenum, the gasification of durene to $CO_2$ and CO could be suppressed, thereby enabling the control of heat generation which would otherwise cause problems in commercial operations of PMDA production. The data also shows that the yield of PMDA was practically independent of the content of Mo within the atomic ratio range of Mo/V=0.3/10-3.0/10 and that the addition of Mo was satisfactorily effective in lowering the degree of gasification of durene.

TABLE 2

| | Atomic ratio of catalyst components | | | Yield of PMDA (wt %) | Degree of gasification ($CO_2$ + CO/durene) (%) | Maximum temperature of catalyst bed (°C.) |
|---|---|---|---|---|---|---|
| | Cr/V | Na/V | Mo/V | | | |
| Comparative Example 1 | 0.5/10 | 0.5/10 | 0/10 | 95 | 39 | 452 |
| Example 4 | 0.5/10 | 0.5/10 | 0.3/10 | 108 | 32 | 446 |
| Example 1 | 0.5/10 | 0.5/10 | 0.5/10 | 113 | 29 | 437 |
| Example 5 | 0.5/10 | 0.5/10 | 1.0/10 | 112 | 27 | 434 |
| Example 6 | 0.5/10 | 0.5/10 | 2.0/10 | 114 | 25 | 431 |
| Example 7 | 0.5/10 | 0.5/10 | 3.0/10 | 113 | 22 | 426 |
| Comparative | 0.5/10 | 0.5/10 | 3.5/10 | 98 | 21 | 425 |

TABLE 2-continued

| Atomic ratio of catalyst components | | | Yield of PMDA | Degree of gasification ($CO_2$ + CO/durene) | Maximum temperature of catalyst bed |
|---|---|---|---|---|---|
| Cr/V | Na/V | Mo/V | (wt %) | (%) | (°C.) |
| Example 2 | | | | | |

EXAMPLE 8

Water (200 cc) was added to vanadium pentoxide (8.0 g) and oxalic acid (22.1 g), and the mixture was held in a hot water bath. To the heated mixture, manganese carbonate (0.5 g), sodium carbonate (232 mg) and molybdic acid (791 mg, 80 wt. % $MoO_3$) were added to prepare an aqueous solution of catalyst components. To this solution, Δ-alumina (80 g; particle size, 3 mmφ) was added and the mixture was concentrated to dryness over a hot water bath with careful stirring. The dried mixture was calcined at 500° C. for 3h under an air stream to prepare a catalyst consisting of 10 V, 0.5 Mn, 0.5 Na and 0.5 Mo in atomic ratio.

The prepared catalyst (60 cc) was packed into a reaction tube having an inside diameter of 1 inch. After immersing the reaction tube in a molten salt bath, a reaction experiment was conducted in the following manner. A feed gas consisting of durene and air at a molar ratio of 0.2:100 was supplied into the reaction tube from the top at a space velocity of 12,000h$^{-1}$ while the molten salt bath was held at 390° C. During the reaction, the temperature of the catalyst bed reached a maximum of 425° C. The reaction gases being generated were withdrawn with a syringe and analyzed by gas chromatography; 27% of durene was found to have been gasified.

As a result of the reaction, pyromellitic dianhydride was produced in a yield of 109 wt. %. The reaction product obtained was analyzed as in Example 1.

EXAMPLE 9

A reaction experiment was conducted as in Example 8 except that the molten salt bath was held at 440° C. and that the concentration of durene in the feed gas (in mol% of air) and the space velocity were adjusted to 0.22 and 10,000h$^{-1}$, respectively.

COMPARATIVE EXAMPLE 3

A catalyst was prepared as in Example 8 except that molybdic acid was not added. The so prepared catalyst was used in a reaction experiment that was conducted as in Example 8.

The results of Example 9 and Comparative Example 3 are shown in Table 3, together with those of Example 8.

any significant change in the yield of PMDA. Comparing the results of Example 8 and Comparative Example 3, one can also see that by adding molybdenum to the catalyst, the reaction temperature in the catalyst bed was lowered by as many as 10° C. while the degree of gasification decreased by 10%.

EXAMPLE 10

Water (200 cc) was added to vanadium pentoxide (8.0 g) and oxalic acid (18 g), and the mixture was held in a hot water bath. To the heated mixture, niobium oxalate (511 as one gram equivalent, 4.49 g), sodium carbonate (139 mg) and molybdic acid (1.58 g, 80 wt. % $MoO_3$) were added to prepare an aqueous solution of catalyst components. This solution was sprayed onto a silicon carbide powder preheated at 200° C. (100 g; average particle sized, 2.5 mmφ) to have the catalyst components supported on the silicon carbide particles. The supported catalyst components were calcined at 500° C. for 3h under an air stream to prepare a catalyst consisting of 10V, 1.0Nb, 0.3Na and 1.0Mo in atomic ratio.

The prepared catalyst (60 cc) was packed into a reaction tube having an inside diameter of 1 inch. After immersing the reaction tube in a molten salt bath, a reaction experiment was conducted in the following manner. A feed gas consisting of durene and air at a molar ratio of 0.24:100 was supplied into the reaction tube from the top at a space velocity of 12,000h$^{-1}$ while the molten salt bath was held at 390° C. During the reaction, the temperature of the catalyst bed reached a maximum of 435° C. The reaction gases being generated were with a syringe and analyzed by gas chromatography; 29% of durene was found to have been gasified.

As a result of the reaction, pyromellitic dianhydride was produced in a yield of 111 wt. %. The reaction product obtained was analyzed by gas chromatography as in Example 1.

COMPARATIVE EXAMPLE 4

A catalyst was prepared as in Example 10 except that molybdic acid was not added. The so prepared catalyst was used in a reaction experiment that was conducted as in Example 10. During the reaction, the temperature of the catalyst bed reached a maximum of 451° C. The reaction gases being generated were withdrawn with a syringe and analyzed by gas chromatography; 37% of durene was found to have been gasified.

TABLE 3

| | Heating temperature (temperature of molten salt bath) (°C.) | Maximum temperature (°C.) | Space velocity h$^{-1}$ | Durene concentration mol% (of air) | PMDA yield (wt %) | Degree of gasification ($CO_2$ + CO/durene) (%) |
|---|---|---|---|---|---|---|
| Example 8 | 390 | 425 | 12,000 | 0.20 | 109 | 27 |
| Example 9 | 440 | 490 | 10,000 | 0.22 | 104 | 34 |
| Comparative Example 3 | 390 | 435 | 12,000 | 0.20 | 94 | 38 |

As one can see from the data in Table 3, the Mo-containing catalyst systems used in Examples 8 and 9 are industrially advantageous catalysts since the setting of heating temperature could be altered without causing As a result of the reaction, pyromellitic dianhydride was produced in a yield of 95 wt. %.

Comparing these results with those obtained in Example 10, one can see that by adding molybdenum to the catalyst, the reaction temperature in the catalyst bed was lowered by as many as 16° C. while the degree of gasification of durene decreased by 8%.

EXAMPLES 11-13

Using the catalyst prepared in Example 10, reaction experiments were conducted as in Example 10 except that the setting of heating temperature was varied.

COMPARATIVE EXAMPLES 5-7

Using the catalyst prepared in Comparative Example 4, reaction experiments were conducted as in Comparative Example 4 except that the setting of heating temperature was varied.

The results of Examples 11-13 and Comparative Examples 5-7 are shown in Table 4, together with those of Example 10 and Comparative Example 4. The data in Table 4 is shown graphically in FIG. 1.

TABLE 4

|  | Heating temperature (°C.) | PMDA yield (wt %) | Degree of gasification ($CO_2$ + CO/durene) (%) |
| --- | --- | --- | --- |
| Example 10 | 390 | 111 | 29 |
| Example 11 | 410 | 109 | 31 |
| Example 12 | 430 | 108 | 32 |
| Example 13 | 460 | 104 | 34 |
| Comparative Example 4 | 390 | 95 | 37 |
| Comparative Example 5 | 410 | 93 | 40 |
| Comparative Example 6 | 430 | 68 | 55 |
| Comparative Example 7 | 460 | 58 | 60 |

The data in Table 4 and FIG. 1 show that the catalysts prepared in accordance with the present invention that comprised V, Nb and Na and which additionally contained molybdenum are industrially advantageous catalysts that can be used over a broad temperature range with consistent results since the setting of heating temperature could be altered without causing any significant change in the yield of PMDA. On the other hand, the comparative catalysts of V-Nb-Na system which did not contain molybdenum as a catalyst component ensured PMDA yields of ca. 100 wt. % within a narrow temperature range but the PMDA yield dropped to very low levels when these catalysts were used at temperatures outside the optimal range. Therefor, the comparative catalysts are not suitable for use in industrial operations.

EXAMPLE 14

Water (200 cc) was added to vanadium pentoxide (8.0 g) and oxalic acid (18 g), and the mixture was held in a hot water bath. To the heated mixture, titanium tetrachloride(835 mg, 1 gram equivalent = 190), sodium carbonate (326 mg) and molybdic acid (1.58 g, 80 wt. % $MoO_3$) were added to prepare an aqueous solution of catalyst components. This solution was sprayed onto a silicon carbide powder preheated at 200° C. (100 g; average particle size, 2.5 mmφ) to have the catalyst components supported on the silicon carbide particles. The supported catalyst components were calcined at 500° C. for 3h under an air stream to prepare a catalyst consisting of 10 V, 0.5 Ti, 0.7 Na and 1.0 Mo in atomic ratio.

The prepared catalyst (60 cc) was packed into a reaction tube having an inside diameter of 1 inch. After immersing the reaction tube in a molten salt bath, a reaction experiment was conducted in the following manner. A feed gas consisting of durene and air at a molar ration of 0.24:100 was supplied into the reaction tube from the top at a space velocity of 14,000h$^{-1}$ while the molten salt bath was held at 370° C. During the reaction, the temperature of the catalyst bed reached a maximum of 415° C. The reaction gases being generated were withdrawn with a syringe and analyzed by gas chromatography; 27% of durene was found to have been gasified.

As a result of the reaction, pyromellitic dianhydride was produced in a yield of 116 wt. %. The reaction product was analyzed by gas chromatography as in Example 1.

COMPARATIVE EXAMPLE 8

A catalyst was prepared as in Example 14 except that molybdic acid was not added. The so prepared catalyst was used in a reaction experiment that was conducted as in Example 14. During the reaction, the temperature of the catalyst bed reached a maximum of 425° C. The reaction gases being generated were withdrawn with a syringe and analyzed by gas chromatography; 37% of durene was found to have been gasified.

As a result of the reaction, pyromellitic dianhydride was produced in a yield of 95 wt. %.

Comparing these results with those obtained in Example 14, one can see that by adding molybdenum to a V-Na-Ti catalyst system, the reaction temperature in the catalyst bed was lowered by as many as 10° C. while the degree of gasification of durene decreased by 8%.

EXAMPLES 15-18

Using the catalyst prepared in Example 14, reaction experiment were conducted as in Example 14 except that the initial setting of heating temperature was varied.

COMPARATIVE EXAMPLES 9-12

Using the catalyst prepared in Comparative Example 8, reaction experiments were conducted as in Example 14 except that the initial setting of heating temperature was varied.

The results of Examples 14-18 and Comparative Examples 8-12 are shown in Table 5. The data in Table 5 is shown graphically in FIG. 2.

TABLE 5

|  | Heating temperature (°C.) | PMDA yield (wt %) | Degree of gasification ($CO_2$ + CO/durene) (%) |
| --- | --- | --- | --- |
| Example 18 | 350 | 90 | 20 |
| Example 14 | 370 | 116 | 27 |
| Example 15 | 390 | 114 | 29 |
| Example 16 | 400 | 110 | 31 |
| Example 17 | 420 | 106 | 33 |
| Comparative Example 12 | 350 | 73 | 25 |
| Comparative Example 8 | 370 | 95 | 37 |
| Comparative Example 9 | 390 | 93 | 39 |
| Comparative Example 10 | 400 | 68 | 56 |

TABLE 5-continued

|  | Heating temperature (°C.) | PMDA yield (wt %) | Degree of gasification ($CO_2$ + CO/durene) (%) |
|---|---|---|---|
| Comparative Example 11 | 420 | 54 | 62 |

The data in table 5 and FIG. 2 show that the catalysts prepared in accordance with the present invention that comprises V, Ti and Na and which additionally contained molybdenum are industrially advantageous catalysts that can be used over a broad temperature range with consistent results since the setting of heating temperature could be altered without causing any significant change in the yield of PMDA. On the other hand, the comparative catalysts of V-Ti-Na system which did not contain molybdenum as a catalyst component ensured PMDA yields of ca. 100% within a narrow temperature range but because of their high sensitivity to temperature, the PMDA yield dropped to very low levels when these catalysts were used at temperatures outside the optimal range. Therefore, the comparative catalysts are not suitable for use in industrial operations.

At the setting temperature less than 360° C. for the catalyst consisting of V-Ti-Na-Mo, the reactivity was decreased and the yield of PMDA was decreased.

COMPARATIVE EXAMPLE 13

A catalyst was prepared as in Example 14 except that titanium tetrachloride, sodium carbonate and molybdic acid were not added. The so prepared catalyst was used in a reaction experiment that was conducted as in Example 1, except that the setting of heating temperature was 420° C.

COMPARATIVE EXAMPLE 14

A catalyst was prepared as in Example 14 except that titanium tetrachloride and sodium carbonate were not added. The so prepared catalyst was used in a reaction experiment that was conducted as in Example 1, except that the setting of heating temperature was 420° C.

COMPARATIVE EXAMPLE 15

A catalyst was prepared as in Comparative Example 14 except that ammonium dihydrogenphosphate (2 g) was added. The so prepared catalyst was used in a reaction experiment that was conducted as in Example 1, except that the setting of heating temperature was 440° C. and the space velocity was $10,000h^{-1}$.

The results of Comparative Example 13-15 are shown in Table 6.

The data in Table 6 of Comparative Example 13-15 showed low yields of PMDA.

TABLE 6

|  | Heating temperature (°C.) | PMDA yield (wt %) | Degree of gasification ($CO_2$ + CO/durene) (%) |
|---|---|---|---|
| Comparative Example 13 | 420 | 57 | 28 |
| Comparative Example 14 | 420 | 15 | 4 |
| Comparative Example 15 | 440 | 10 | 3 |

EXAMPLES 19-23

Water (200 cc) was added to vanadium pentoxide(8.0 g) and oxalic acid (22.1 g), and the mixture was held in a hot water bath. To the heated mixture, sodium carbonate, molybdic acid (80wt % $MoO_3$), niobium oxalate, titanium tetrachloride, manganese carbonate and ammonium chromate were added with the amounts described at Table 7 to prepare an aqueous solution of catalyst components. To this solution, α-alumina (80 g; particle size, 3 mmφ) was added and the mixture was concentrated to dryness over a hot water bath with careful stirring. The dried mixture was calcined for 6h under an air stream to prepare catalysts.

The atomic ratio of catalyst components of the so prepared catalysts were described at Table 8.

The prepared catalyst (60 cc) was packed into a reaction tube having an inside diameter of 1inch. After immersing the reaction tube in a molten salt bath, a reaction experiment was conducted in the following manner described at Table 9.

The results are shown in Table 9.

TABLE 7

|  | sodium carbonate (mg) | molybdic acid (g) | niobium oxalate (g) | titanium tetrachloride (mg) | manganese carbonate (mg) | ammonium chromate (mg) |
|---|---|---|---|---|---|---|
| Example 19 | 93 | 1.58 | 2.24 | 334 | 200 | 257 |
| Example 20 | 186 | 2.37 | 4.48 | 668 | 0 | 0 |
| Example 21 | 232 | 1.10 | 5.37 | 0 | 501 | 0 |
| Example 22 | 139 | 1.58 | 0 | 501 | 1000 | 0 |
| Example 23 | 139 | 1.58 | 3.58 | 668 | 0 | 400 |

TABLE 8

|  | Atomic ratio of catalyst components | | | | | |
|---|---|---|---|---|---|---|
|  | Na/V | Mo/V | Cr/V | Mn/V | Nb/V | Ti/V |
| Example 19 | 0.2/10 | 1.0/10 | 0.2/10 | 0.2/10 | 0.5/10 | 0.2/10 |
| Example 20 | 0.4/10 | 1.5/10 | 0 | 0 | 1.0/10 | 0.4/10 |
| Example 21 | 0.5/10 | 0.7/10 | 0 | 0.5/10 | 1.2/10 | 0 |
| Example 22 | 0.3/10 | 1.0/10 | 0 | 1.0/10 | 0 | 0.3/10 |
| Example 23 | 0.3/10 | 1.0/10 | 0.3/10 | 0 | 0.8/10 | 0.4/10 |

TABLE 9

|  | Heating temperature (temperature of molten salt bath) (°C.) | Maximum temperature (°C.) | Space velocity $h^{-1}$ | Durene concentration mol % (of air) | PMDA yield (wt %) | Degree of gasification ($CO_2$ + CO/ durene) (%) |
|---|---|---|---|---|---|---|
| Example 19 | 395 | 433 | 11,000 | 0.2 | 113 | 27 |
| Example 20 | 410 | 410 | 14,000 | 0.2 | 112 | 26 |
| Example 21 | 440 | 440 | 12,000 | 0.15 | 110 | 30 |

TABLE 9-continued

| | Heating temperature (temperature of molten salt bath) (°C.) | Maximum temperature (°C.) | Space velocity h$^{-1}$ | Durene concentration mol % (of air) | PMDA yield (wt %) | Degree of gasification (CO$_2$ + CO/ durene) (%) |
|---|---|---|---|---|---|---|
| Example 22 | 390 | 435 | 12,000 | 0.20 | 109 | 31 |
| Example 23 | 390 | 466 | 12,000 | 0.25 | 108 | 32 |

The results of Example 19-23 showed that the catalyst having the mixture of additional components of chromium oxide, manganese oxide, niobium oxide and titanium oxide, like the catalyst having one additional component used Example 1-18, resulted in high PMDA yield with a good catalytic activity without increase of the degree of gasification.

Using the catalyst described hereinabove, the process of the present invention is capable of producing pyromellitic acid dianhydride in high yield from durene whose price has dropped considerably as a result of its high-volume supply that became possible by the advances in the petrochemical industry. In addition, this process can be performed over a broad optimal temperature range while suppressing the heat generation in the catalyst bed which would otherwise cause problems in commercial operations.

What is claimed is:

1. A catalyst for use in the production of pyromellitic dianhydride by vapor-phase oxidation of durene, said catalyst comprising an inert support carrying vanadium oxide, sodium oxide, molybdenum oxide, and at least one additional component selected from the group consisting of chromium oxide, manganese oxide, niobium oxide and titanium oxide, with the atomic ratios of the metallic elements in the supported oxides being within the following ranges: Na/V=0.1/10–1.0/10, Mo/V=0.3/10–3.0/10, Cr/V=0.2/10–2.0/10, Mn/V=0.1/10–1.5/10, Nb/V=0.5/10–3.0/10, and Ti/V=0.1/10–1.0/10.

2. A catalyst according to claim 1 wherein said inert support is α-alumina or silicon carbide.

3. A catalyst according to claim 1 wherein the catalyst components are carried on said inert support in such amounts that vanadium pentoxide is supported in a weight of 3–5% of the weight of the support.

4. A catalyst according to claim 1 wherein said additional component is niobium oxide.

5. A catalyst according to claim 1 wherein said additional component is titanium oxide.

* * * * *

UNITED STATES PATENT AND TRADEMARK OFFICE
CERTIFICATE OF CORRECTION

PATENT NO. : 5,001,100
DATED : March 19, 1991
INVENTOR(S) : N. Enomoto, et. al.

It is certified that error appears in the above-indentified patent and that said Letters Patent is hereby corrected as shown below:

Column 16, Claim 3, line 4, change "3-5%" to --3-15%--.

Signed and Sealed this

Ninth Day of November, 1993

Attest:

BRUCE LEHMAN

Attesting Officer        Commissioner of Patents and Trademarks